US008153138B2

(12) United States Patent
Sutter et al.

(10) Patent No.: US 8,153,138 B2
(45) Date of Patent: *Apr. 10, 2012

(54) RECOMBINANT MVA VIRUS

(75) Inventors: Gerd Sutter, Münich (DE); Marion Ohlmann, Münich (DE); Volker Erfle, Münich (DE)

(73) Assignee: GSF-Forschungszentrum fur Umwelt und Gesundheit GmbH, Oberschleissheim (DE)

( * ) Notice: Subject to any disclaimer, the term of this patent is extended or adjusted under 35 U.S.C. 154(b) by 1148 days.

This patent is subject to a terminal disclaimer.

(21) Appl. No.: 11/522,889

(22) Filed: Sep. 19, 2006

(65) Prior Publication Data

US 2010/0266630 A1    Oct. 21, 2010

Related U.S. Application Data

(60) Division of application No. 10/147,284, filed on May 15, 2002, now Pat. No. 7,198,934, which is a continuation of application No. 09/002,443, filed on Jan. 2, 1998, now Pat. No. 6,440,422, which is a continuation of application No. PCT/EP96/02926, filed on Jul. 3, 1996.

(30) Foreign Application Priority Data

Jul. 4, 1995  (DK) ..................... 0782/95

(51) Int. Cl.
*A61K 39/12* (2006.01)
(52) U.S. Cl. ............. 424/232.1; 424/184.1; 424/204.1
(58) Field of Classification Search .............. None
See application file for complete search history.

(56) References Cited

U.S. PATENT DOCUMENTS

| | | | |
|---|---|---|---|
| 5,185,146 | A | 2/1993 | Altenburger |
| 5,221,610 | A | 6/1993 | Montagnier et al. |
| 5,676,950 | A | 10/1997 | Small, Jr. et al. |
| 5,679,511 | A | 10/1997 | Kwon |

FOREIGN PATENT DOCUMENTS

| | | |
|---|---|---|
| CH | 568 392 | 10/1975 |
| EP | 324350 A1 | 7/1989 |

OTHER PUBLICATIONS

Alexander et al. (Journal of Virology, 1992 vol. 66 No. 5, pp. 2934-2942).*
Sutter et al., "A Recombinant Vector Derived from the Host Range-Restricted and Highly Attenuated MVA Strain of Vaccinia Virus Stimulates Protective Immunity in Mice to Influenza Virus," *Vaccine*, 12(11):1032-1040 (1994).
Hirsch, et al., "Limited virus Replication Following SIV Challenge of Macaques Immunized with Attenuated MVA Vaccinia Expressing SIVsm env and gag-pol," Vaccines, Cold Spring Laboratory Press, USA, 95:195-200 (1995).
Mayr, et al., "Abstammung, Eigenschaften and Verwendung des Attenuierten Vaccinia-Stammes MVA," *Infection*, 3:6-14 (1975) Abstract Only.
Mayr et al., "The Smallpox Vaccination Strain MVA: Marker, Genetic Structure, Experience Gained with the Parenteral Vaccination and Behavior in Organisms with a Debilitated Defence Mechanism," *Zbl. Bakt. Hyg., I Abt. Org, B*, 167:375-390 (1978) Abstract Only.
Meyer et al., "Mapping of Deletions in the Genome of the Highly Attenuated Vaccinia Virus MVA and Their Influence on Virulence," *J. Gen. Virol.*, 72:1031-1038 (1991).
Stickl et al., "MVA-Stufenimpfung Gegen Pocken," *Dtsch. Med. Wschr.*, 99:2386-2392 (1974) Abstract Only.
Sutter and Moss, "Nonreplicating Vaccinia Vector Efficiently Expresses Recombinant Genes," *Proc. Natl. Acad. Sci., USA*, 89:10847-10851 (1992).
Sutter and Moss, "Novel Vaccinia Vector Derived from the Host Range Restricted and Highly Attenuated Strain of Vaccinia Virus," *Dev. Biol. Stand. Basel, Karger*, 84:195-200 (1995).
Altenburger et al., "Partial Deletion of the Human Host Range Gene in the Attenuated Vaccinia Virus MVA," *Arch. Virol.*, 105:15-27 (1989).
Hirsch et al., "Patterns of Viral Replication Correlate with Outcome in Simian Immunodeficiency Virus (SIV)-Infected Macaques: Effect of Prior Immunization with a Trivalent SIV Vaccine in Modified Vaccinia Virus Ankara," *J. Virol.*, 70(6):3741-3752 (1996).
Wyatt et al., "Replication-Deficient Vaccinia Virus Encoding Bacteriophage T7 RNA Polymerase for Transient Gene Expression in Mammalian Cells," *Virol.*, 210:202-205 (1995).
Carroll et al., "*E. coli* β-glucuronidase (GUS) as a Marker for Recombinant Vaccinia Viruses," *Biotechniques*, 19:352-355 (1995).
NTIS Accession No. PB89144802, "Novel Inhibitor of HIV Infection."
NTIS Accession No. PB88201363, "Novel Recombinant Vaccinia Virus Expression Vectors and Method of Selecting Same."
NTIS Accession No. PB88192059, "A Synthetic Antigen Evoking Anti-HIV Response."
Sutter et al., "Non-Replicating Vaccinia Vector Efficiently Expresses Bacteriophage T7 RNA Polymerase," *FEBS Letters*, 371:9-12 (1995).
Greenspan et al., "Defining Epitopes: It's Not as Easy as it Seems," *Natl. Biotechnology*, 7:936-937 (1999).
Bowie et al., "Deciphering the Message in Protein Sequences: Tolerance to Amino Acid Substitutions," *Science*, 257:1306-1310 (1990).
Scheiflinger et al., "Evaluation of the Thyrmidine Kinase (tk) Locus as an Insertion Site in the Highly Attenuated Vaccinia MVA Strain," *Arch. Virol.*, 141:663-669 (1996).
Antoine et al., "Characterization of the Vaccinia MVA Hemagglutinin Gene Locus and its Evaluation as an Insertion Site for Foreign Genes," *Gene*, 177:43-46 (1996).

* cited by examiner

*Primary Examiner* — Robert A Zeman
(74) *Attorney, Agent, or Firm* — Law Office of Salvatore Arrigo and Scott Lee, LLP

(57) ABSTRACT

The present invention relates to recombinant vaccinia viruses derived from the modified vaccinia virus Ankara (MVA) and containing and capable of expressing foreign genes which are inserted at the site of a naturally occurring deletion in the MVA genome, and the use of such recombinant MVA viruses for the production of polypeptides, e.g. antigens or therapeutic agents, or viral vectors for gene therapy, and the use of such recombinant MVA viruses encoding antigens as vaccines.

10 Claims, 6 Drawing Sheets

SEQUENCE LISTING

<160> NUMBER OF SEQ ID NOS: 8

<210> SEQ ID NO 1
<211> LENGTH: 33
<212> TYPE: DNA
<213> ORGANISM: Unknown
<220> FEATURE:
<223> OTHER INFORMATION: Primer for left 660-bp of MVA DNA flanking the
      site of a 2500-bp deletion in the HindIII N
      fragment of the MVA genome

<400> SEQUENCE: 1
cagcagggta ccctcatcgt acaggacgtt ctc                              33

<210> SEQ ID NO 2
<211> LENGTH: 42
<212> TYPE: DNA
<213> ORGANISM: Unknown
<220> FEATURE:
<223> OTHER INFORMATION: Primer for left 660-bp of MVA DNA flanking the
      site of a 2500-bp deletion in the HindIII N
      fragment of the MVA genome

<400> SEQUENCE: 2
cagcagcccg ggtattcgat gattattttt aacaaaataa ca                    42

<210> SEQ ID NO 3
<211> LENGTH: 36
<212> TYPE: DNA
<213> ORGANISM: Unknown
<220> FEATURE:
<223> OTHER INFORMATION: Primer for right 550-bp of MVA DNA flanking the
      site of a 2500-bp deletion in the HindIII N
      fragment of the MVA genome

<400> SEQUENCE: 3
cagcagctgc aggaatcatc cattccactg aatagc                           36

<210> SEQ ID NO 4
<211> LENGTH: 36
<212> TYPE: DNA
<213> ORGANISM: Unknown
<220> FEATURE:
<223> OTHER INFORMATION: Primer for right 550-bp of MVA DNA flanking the
      site of a 2500-bp deletion in the HindIII N
      fragment of the MVA genome

<400> SEQUENCE: 4
cagcaggcat gccgacgaac aaggaactgt agcaga                           36

<210> SEQ ID NO 5
<211> LENGTH: 33
<212> TYPE: DNA
<213> ORGANISM: Unknown
<220> FEATURE:
<223> OTHER INFORMATION: PCR primer for amplifying E. coli LacZ open
      reading frame

<400> SEQUENCE: 5
cagcaggtcg accccgaccg ccttactgcc gcc                              33

<210> SEQ ID NO 6

```
<211> LENGTH: 33
<212> TYPE: DNA
<213> ORGANISM: Unknown
<220> FEATURE:
<223> OTHER INFORMATION: PCR primer for amplifying E. coli LacZ open
      reading frame

<400> SEQUENCE: 6 gggggctgc agatggtagc gaccggcgct cag                                  33

<210> SEQ ID NO 7
<211> LENGTH: 39
<212> TYPE: DNA
<213> ORGANISM: Unknown
<220> FEATURE:
<223> OTHER INFORMATION: Primer for amplifying a 648bp DNA fragment
      containing the entire nef gene of HIV-1 LAI

<400> SEQUENCE: 7
cagcagggat ccatgggtgg caagtggtca aaaagtagt                           39

<210> SEQ ID NO 8
<211> LENGTH: 39
<212> TYPE: DNA
<213> ORGANISM: Unknown
<220> FEATURE:
<223> OTHER INFORMATION: Primer for amplifying a 648bp DNA fragment
      containing the entire nef gene of HIV-1 LAI

<400> SEQUENCE: 8
cagcagggat ccatgtcagc agttcttgaa gtactccgg                           39
```

RECOMBINANT MVA VIRUS

RELATED APPLICATION(S)

This application is a division of U.S. application Ser. No. 10/147,284, filed May 15, 2002 now U.S. Pat. No. 7,198,934, which is a continuation of U.S. application Ser. No. 09/002,443, filed Jan. 2, 1998 now U.S. Pat. No. 6,440,422, which is a continuation of International Application No. PCT/EP96/02926, which designated the United States and was filed on Jul. 3, 1996, published in English, which claims the benefit of Danish Patent Application No. DK 0782/95, filed Jul. 4, 1995. The entire teachings of the above application(s) are incorporated herein by reference

BACKGROUND OF THE INVENTION

Vaccinia virus, a member of the genus Orthopoxvirus in the family of Poxyiridae, was used as live vaccine to immunize against the human smallpox disease. Successful world-wide vaccination with vaccinia virus culminated in the eradication of variola virus, the causative agent of the smallpox (The global eradication of smallpox. Final report of the global commission for the certification of smallpox eradication. History of Public Health, No. 4, Geneva: World Health Organization, 1980). Since that WHO declaration, vaccination has been universally discontinued except for people at high risk of poxvirus infections (e.g. laboratory workers).

More recently, vaccinia viruses have also been used to engineer viral vectors for recombinant gene expression and for the potential use as recombinant live vaccines (Mackett, M. et al., *P.N.A.S. USA,* 79:7415-7419 (1982); Smith, G. L et al., *Biotech. and Genetic Engineering Reviews* 2:383-407, (1984)). This entails DNA sequences (genes) which code for foreign antigens being introduced, with the aid of DNA recombination techniques, into the genome of the vaccinia viruses. If the gene is integrated at a site in the viral DNA which is non-essential for the life cycle of the virus, it is possible for the newly produced recombinant vaccinia virus to be infectious, that is to say able to infect foreign cells and thus to express the integrated DNA sequence (EP Patent Applications No. 83,286 and No. 110,385)). The recombinant vaccinia viruses prepared in this way can be used, on the one hand, as live vaccines for the prophylaxis of infectious diseases, on the other hand, for the preparation of heterologous proteins in eukaryotic cells.

Recombinant vaccinia virus expressing the bacteriophage T7 RNA polymerase gene allowed the establishment of widely applicable expression systems for the synthesis of recombinant proteins in mammalian cells (Moss, B., et al., *Nature,* 348:91-92 (1990)). In all protocols, recombinant gene expression relies on the synthesis of the T7 RNA polymerase in the cytoplasm of eukaryotic cells. Most popular became a protocol for transient-expression (Fuerst, T. R., et al., *Proc. Natl. Acad. Sci. USA,* 83:8122-8126 (1986) and U.S. Pat. No. 7,648,971)). First, a foreign gene of interest is inserted into a plasmid under the control of the T7 RNA polymerase promoter. In the following, this plasmid is introduced into the cytoplasm of cells infected with a recombinant vaccinia virus producing T7 RNA polymerase using standard transfection procedures.

This transfection protocol is simple because no new recombinant viruses need to be made and very efficient with greater than 80% of the cells expressing the gene of interest (Elroy-Stein, O. and Moss, B., *Proc. Natl. Acad. Sci. USA,* 87:6743-6747 (1990)). The advantage of the vaccinia virus/T7 RNA polymerase hybrid system over other transient expression systems is very likely its independence on the transport of plasmids to the cellular nucleus. In the past, the system has been extremely useful for analytical purposes in virology and cell biology (Buonocore, L. and Rose, J. K, *Nature,* 345:625-628, (1990); Pattnaik, A. K and Wertz, G. W., *Proc. Natl. Acad. Sci. USA,* 88:1379-1383 (1991); Karschin, A. et al., *FEBS Lett.* 278: 229-233 (1991), Ho, B. Y. et al., *FEBS Lett.,* 301:303-306 (1992); Buchholz, C. J. et al., *Virology,* 204: 770-776 (1994)). However, important future applications of the vaccinia virus/T7 RNA polymerase hybrid system, as e.g. to generate recombinant proteins or recombinant viral particles for novel therapeutic or prophylactic approaches in humans, might be hindered by the productive replication of the recombinant vaccinia vector.

Vaccinia virus is infectious for humans and upon vaccination during the smallpox eradication campaign occasional serious complications were observed. The best overview about the incidence of complications is given by a national survey in the United States monitoring vaccination of about 12 million people with a vaccine based on the New York City Board of Health strain of vaccinia virus (Lane, J. et al. *New Engl. J. Med.,* 281:1201-1208, (1969)). Therefore the most exciting possibility to use vaccinia virus as vector for the development of recombinant live vaccines has been affected by safety concerns and regulations. Furthermore, most of the recombinant vaccinia viruses described in the literature are based on the Western Reserve strain of vaccinia virus. On the other hand, it is known that this strain has a high neurovirulence and is thus poorly suited for use in humans and animals (Morita et al., *Vaccine,* 5:65-70 (1987)).

For vector applications health risks would be lessened by the use of a highly attenuated vaccinia virus strain. Several such strains of vaccinia virus were especially developed to avoid undesired side effects of smallpox vaccination. Thus, the modified vaccinia virus Ankara (MVA) has been generated by long-term serial passages of the Ankara strain of vaccinia virus (CVA) on chicken embryo fibroblasts (for review see Mayr, A., et al., *Infection,* 3:6-14 (1975); Swiss Patent No. 568,392)). The MVA virus was deposited in compliance with the requirements of the Budapest Treaty at CNCM (Institut Pasteur, Collection Nationale de Cultures Microorganisms, 25, rue du Docteur Roux, 75724 Paris Cedex 15) on Dec. 15, 1987 under Depositary No. I-721. MVA is distinguished by its great attenuation, that is to say by diminished virulence or infectiosity while maintaining good immunogenicity. The MVA virus has been analyzed to determine alterations in the genome relative to the wild CVA strain. Six major deletions of genomic DNA (deletion I, II, III, IV, V, and VI) totaling 31,000 base pairs have been identified (Meyer, H., et al., *J. Gen. Virol.* 72:1031-1038 (1991)). The resulting MVA virus became severely host cell restricted to avian cells.

Furthermore, MVA is characterized by its extreme attenuation. When tested in a variety of animal models, MVA was proven to be avirulent even in immunosuppressed animals. More importantly, the excellent properties of the MVA strain have been demonstrated in extensive clinical trials (Mayr et al., Zbl. *Bakt. Hyg. I, Abt. Org. B* 167:375-390 (1987), Stickl et al., *Dtsch. med. Wschr.* 99:2386-2392 (1974)). During these studies in over 120,000 humans, including high risk patients, no side effects were associated with the use of MVA vaccine.

MVA replication in human cells was found to be blocked late in infection preventing the assembly to mature infectious virions. Nevertheless, MVA was able to express viral and recombinant genes at high levels even in non-permissive cells and was proposed to serve as an efficient and exceptionally safe gene expression vector (Sutter, G. and Moss, B., *Proc. Natl. Acad. Sci. USA* 89:10847-10851 (1992)). Recently, novel vaccinia vector systems were established on the basis of MVA, having foreign DNA sequences inserted at the site of deletion III within the MVA genome or within the TK gene (Sutter, G. and Moss, B. *Dev. Biol. Stand. Basel*, Karger 84:195-200 (1995) and U.S. Pat. No. 5,185,146)).

To further exploit the use of MVA a novel possible way to introduce foreign genes by DNA recombination into the MVA strain of vaccinia virus has been sought. Since the intention was not to alter the genome of the MVA virus, it was necessary to use a method which complied with this requirement. According to the present invention a foreign DNA sequence was recombined into the viral DNA precisely at the site of a naturally occurring deletion in the MVA genome.

SUMMARY OF THE INVENTION

The present invention thus, inter alia, comprises the following, alone or in combination:

A recombinant MVA virus containing and capable of expressing at least one foreign gene inserted at the site of a naturally occurring deletion within the MVA genome;

a recombinant MVA virus as above containing and capable of expressing at least one foreign gene inserted at the site of deletion II within the MVA genome;

a recombinant MVA virus as above wherein the foreign gene codes for a marker, a therapeutic gene or an antigenic determinant;

a recombinant MVA virus as above wherein the foreign gene codes for an antigenic determinant from a pathogenic virus, a bacteria, or other microorganism, or from a parasite, or a tumor cell;

a recombinant MVA virus as above wherein the foreign gene codes for an antigenic determinant from *Plasmodium Falciparum*, Mycobacteria, Herpes virus, influenza virus, hepatitis, or human immunodeficiency viruses.

a recombinant MVA virus as above wherein the antigenic determinant is HIV nef or human tyrosinase;

a recombinant MVA virus as above which is MVA-LAInef or MVA-hTYR;

a recombinant MVA virus as above wherein the foreign gene codes for T7 RNA polymerase;

a recombinant MVA virus as above which is MVA-T7 pol;

a recombinant MVA virus as above wherein the foreign gene is under transcriptional control of the vaccinia virus early/late promoter P7.5;

recombinant MVA viruses as above essentially free from viruses being able to replicate in human cells;

the use of a recombinant MVA virus as above for the transcription of DNA sequences under transcriptional control of a T7 RNA polymerase promoter;

a eukaryotic cell infected by a recombinant MVA virus as any above;

a cell infected by a recombinant MVA virus as above wherein the foreign gene code for T7 RNA polymerase;

a cell infected by a recombinant MVA virus as above wherein the foreign gene code for T7 RNA polymerase, additionally containing one or more expression vectors carrying one or more foreign genes under transcriptional control of a T7 RNA polymerase promoter;

the use of cells as above for the production of the polypeptides encoded by said foreign genes comprising:
a) culturing said cells under suitable conditions, and
b) isolating the polypeptides encoded by said foreign genes.

a cell infected by a recombinant MVA virus as above wherein the foreign gene code for T7 RNA polymerase, additionally containing expression vectors carrying viral genes, and/or a viral vector construct encoding the genome of a viral vector under transcriptional control of a T7 RNA polymerase promoter;

the use of a cells as above for the production viral particles comprising:
a) culturing said cells under suitable conditions, and
b) isolating the viral particles;

a cell infected by a recombinant MVA virus as above wherein the foreign gene code for T7 RNA polymerase, additionally containing
a) an expression vector carrying a retroviral vector construct capable of infecting and directing the expression in target cells of one or more foreign genes carried by said retroviral vector construct, and
b) one or more expression vectors carrying the genes encoding the polypeptides required for the genome of said retroviral vector construct to be packaged under transcriptional control of a T7 RNA polymerase promoter;

the use of cells as above for the production of retroviral particles comprising
a) culturing said cells under suitable conditions, and
b) isolating the retroviral particles;

a vaccine containing a recombinant MVA virus as above wherein the foreign gene code for an antigenic determinant in a physiologically acceptable carrier;

the use of a recombinant MVA virus as above wherein the foreign gene code for an antigenic determinant preparation of a vaccine;

the use of a vaccine as above for the immunization of a living animal body, including a human;

the use of a vaccine as above containing MVA-LAInef for the prevention or treatment of HIV infection or AIDS;

the use of a vaccine as above containing MVA-hTYR for the prevention or treatment of melanomas;

a vaccine comprising as a first component, a recombinant MVA virus as above wherein the foreign gene code for T7 RNA polymerase in a physiologically acceptable carrier, and as a second component a DNA sequence carrying an antigenic determinant under transcriptional control of a T7 RNA polymerase promoter in a physiologically acceptable carrier, the two components being contained together or separate;

the use of a vaccine as above for the immunization of a living animal body, including a human, comprising inoculation of said living animal body, including a human, with the first and second component of the vaccine either simultaneously or with a timelag using the same inoculation site; and The term "gene" means any DNA sequence which codes for a protein or peptide.

The term "foreign gene" means a gene inserted in a DNA sequence in which it is not normally found.

The foreign gene can be a marker gene, a therapeutic gene, a gene encoding an antigenic determinant, or a viral gene, for example. Such genes are well known in the art.

DETAILED DESCRIPTION OF THE INVENTION

Figure 1:
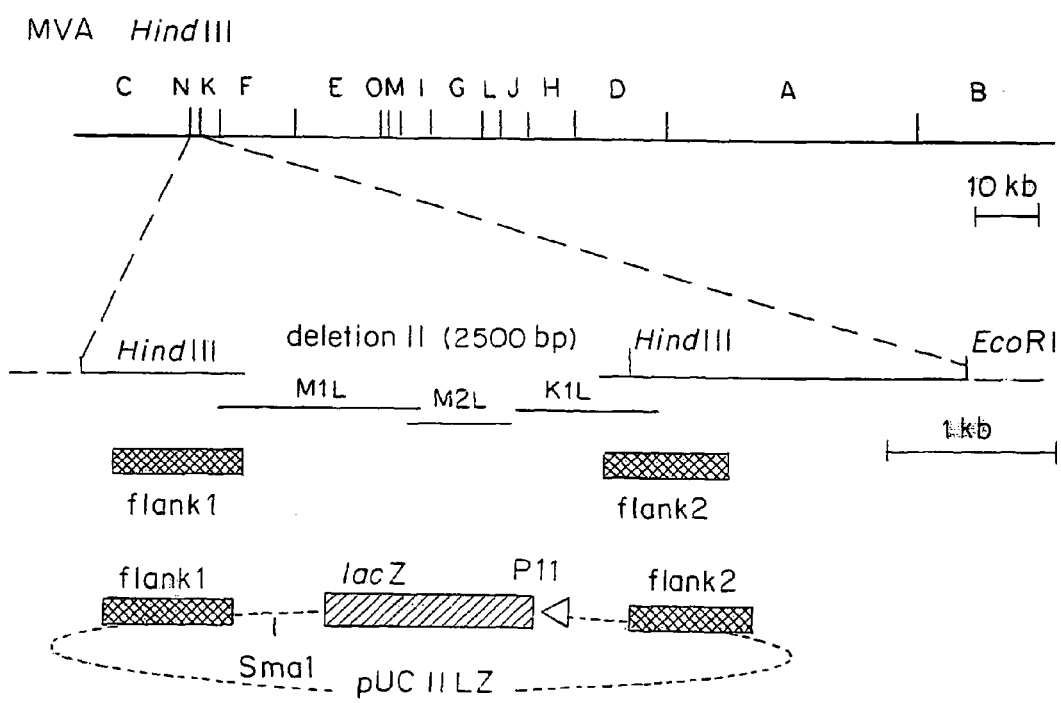
FIG. 1 is a schematic map of the genome of MVA and plasmid for insertion of foreign DNA by homologous recombination: HindIII restriction sites within the genome of MVA are indicated at the top; the 900-bp HindIII-HindIII N fragment that overlaps the junction of deletion II within the MVA genome is shown; MVA DNA sequences adjacent to deletion II (flank 1 and flank 2) were amplified by PCR and used for the construction of insertion plasmid pUC II LZ.

It is an object of the present invention to provide a recombinant MVA virus which can serve as an efficient and exceptionally safe expression vector.

Another object of the present invention is to provide a simple, efficient and safe method for the production of polypeptides, e.g. antigens or therapeutic agents, recombinant viruses for vaccines and viral vectors for gene therapy.

Still another object of the present invention is to provide an expression system based on a recombinant MVA virus expressing T7 RNA polymerase, and methods for the production of polypeptides, e.g. antigens or therapeutic agents, or for generating viral vectors for gene therapy or vaccines, based on this expression system.

The Present Invention

Modified vaccinia virus Ankara (MVA), a host range restricted and highly attenuated vaccinia virus strain, is unable to multiply in human and most other mammalian cell lines tested. But since viral gene expression is unimpaired in non-permissive cells the recombinant MVA viruses according to the invention may be used as exceptionally safe and efficient expression vectors.

Recombinant Mva Viruses Encoding An Antigenic Determinant

In one embodiment, the present invention relates to recombinant MVA vaccinia viruses which contain a gene which codes for a foreign antigen, preferably of a pathogenic agent, and vaccines containing such a virus in a physiologically acceptable form. The invention also relates to methods for the preparation of such recombinant MVA vaccinia viruses or vaccines, and to the use of these vaccines for the prophylaxis of infections caused by such pathogenic agents.

In a preferred embodiment of the invention, the foreign gene inserted in the MVA virus is a gene encoding HIV nef.

We have constructed recombinant MVA viruses that allow expression of the HIV-1 nef gene under the control of the vaccinia virus early/late promoter P7.5. The regulatory Nef protein of primate lentiviruses is synthesized early in the viral replication cycle and has been shown to be essential for high titer virus replication and disease induction in vivo. This suggests that HIV Nef might play a crucial role in AIDS pathogenesis. The molecular mechanism(s) by which Nef contributes to increased viral infectivity and to HIV pathogenicity need to be further elucidated. However, Nef is immunogenic and Nef-specific antigen can be used as a vaccine against HIV infection and AIDS.

In this context, the recombinant MVA virus expressing the HIV nef gene can be used for immunization of human beings, on one hand, as a prophylactic vaccine against human HIV, and on the other hand, for immunotherapy of HIV infected or AIDS patients. Furthermore, the recombinant MVA virus expressing the HIV nef gene can be used for the production of recombinant HIV Nef protein.

In another preferred embodiment of the invention the foreign gene inserted in the MVA virus is a gene encoding human tyrosinase.

We have constructed recombinant MVA viruses that allow expression of the human tyrosinase gene under the control of the vaccinia virus early/late promoter P7.5. Recently, human tyrosinase was identified as a melanoma-specific tumor antigen that allows generation of anti-tumor cytolytic T-lymphocytes (Beichard, V., et al., *J. Exp. Med.*, 178:489-495 (1993)). Since among normal cells, only melanocytes appear to express the tyrosinase gene, tyrosinase is a useful target antigen for immunotherapy of melanomas. Therefore, the recombinant MVA virus expressing the human tyrosinase gene can be used in melanoma patients to induce immune responses that provoke tumor rejection or prevent metastasis. Recombinant MVA virus expressing the human tyrosinase gene can be used directly as an anti-melanoma vaccine, or the virus can be used to prepare anti-melanoma vaccines. In one example, the recombinant MVA virus expressing the human tyrosinase gene can be used for the production of recombinant tyrosinase protein which is used as antigen in vaccine preparations. In another example, using the recombinant MVA virus expressing the human tyrosinase gene as expression vector, cells derived from a tumor patient can be modified in vitro to express tyrosinase and then transferred back to the patient to induce anti-tumor immune responses. A vaccine prepared on the basis of recombinant MVA expressing the human tyrosinase gene can be used either parenterally or locally at the site of the tumor. To prevent tumor metastasis or to phenotypically change the tumor e.g. in size, shape, consistency, vascularization or other features. A vaccine prepared on the basis of recombinant MVA expressing the human tyrosinase gene can be used before, during, or after surgical extirpation of the tumor.

For the preparation of vaccines, the MVA vaccinia viruses according to the invention are converted into a physiologically acceptable form. This can be done based on the experience in the preparation of MVA vaccines used for vaccination against smallpox (as described by Stickl, H. et al., *Dtsch. med. Wschr.* 99:2386-2392 (1974)). Typically, about $10^6$-$10^8$ particles of the recombinant MVA are freeze-dried in 100 ml of phosphate-buffered saline (PBS) in the presence of 2% peptone and 1% human albumin in an ampoule, preferably a glass ampoule. The lyophilisate can contain extenders (such as mannitol, dextran, sugar, glycine, lactose or polyvinylpyrrolidone) or other aids (such as antioxidants, stabilizers, etc.) suitable for parenteral administration. The glass ampoule is then sealed and can be stored, preferably at temperatures below −20° C., for several months.

For vaccination or therapy the lyophilisate can be dissolved in 0.1 to 0.5 ml of an aqueous solution, preferably physiological saline, and administered either parenterally, for example by intramuscular inoculation or locally, for example by inoculation into a tumor or at the site of a tumor. Vaccines or therapeutics according to the invention are preferably injected intramuscularly (Mayr, A. et al., *Zbl. Bakt. Hyg., I. Abt. Orig. B* 167:375-390 (1978)). The mode of administration, the dose and the number of administrations can be optimized by those skilled in the art in a known manner. It is expedient where appropriate to administer the vaccine several times over a lengthy period in order to obtain appropriate immune responses against the foreign antigen.

The Use of Recombinant MVA Viruses for the Production of Heterologous Polypeptides The recombinant MVA vaccinia viruses according to the invention can also be used to prepare heterologous polypeptides in eukaryotic cells. This entails cells being infected with the recombinant vaccinia viruses. The gene which codes for the foreign polypeptide is expressed in the cells, and the expressed heterologous polypeptide is isolated. The methods to be used for the production of such heterologous polypeptides are generally known to those skilled in the art (EP-A-206,920 and EP-A-205,939). The polypeptides produced with the aid of the recombinant MVA viruses are, by reason of the special properties of the MVA viruses, more suitable for use as medicaments in humans and animals.

Recombinant MVA Viruses Encoding T7 RNA Polymerase and the Use Thereof for the Expression of DNA Sequences Under Transcriptional Control of a T7 RNA Polymerase Promoter In a further embodiment of the present invention we have constructed recombinant MVA viruses that allow expression of the bacteriophage T7 RNA polymerase gene under the control of the vaccinia virus early/late promoter P7.5. The usefulness of MVA-T7pol recombinant viruses as expression system has been tested in transient transfection assays to induce expression of recombinant genes under the control of a T7 RNA polymerase promoter. Using the *E. coli* chloramphenicol acetyltransferase (CAT) gene as a reporter gene we found that MVA-T7pol induced CAT gene expression as effectively as a vaccinia/T7pol recombinant virus derived from the replication-competent WR strain of vaccinia virus.

The MVA/T7 polymerase hybrid system according to the invention can thus be used as a simple, efficient and safe mammalian expression system for production of polypeptides in the absence of productive vaccinia virus replication.

This expression system can also be used for generating recombinant viral particles for vaccination or gene therapy by transformation of cell lines infected with recombinant MVA expressing T7 RNA polymerase, with DNA-constructs containing all or some of the genes, and the genome or recombinant genome necessary for generating viral particles, e.g MVA particles or retroviral particles, under transcriptional control of a T7 RNA polymerase promoter.

Retroviral vector systems consist of two components:
1) the retroviral vector itself is a modified retrovirus (vector plasmid) in which the genes encoding for the viral proteins have been replaced by therapeutic genes and marker genes to be transferred to the target cell. Since the replacement of the genes encoding for the viral proteins effectively cripples the virus it must be rescued by the second component in the system which provides the missing viral proteins to the modified retrovirus.

The second component is:
2) a cell line that produces large quantities of the viral proteins, however lacks the ability to produce replication competent virus. This cell line is known as the packaging cell line and consists of a cell line transfected with one or more plasmids carrying the genes (genes encoding the gag, pol and env polypeptides) enabling the modified retroviral vector to be packaged.

To generate the packaged vector, the vector plasmid is transfected into the packaging cell line. Under these conditions the modified retroviral genome including the inserted therapeutic and marker genes is transcribed from the vector plasmid and packaged into the modified retroviral particles (recombinant viral particles). This recombinant virus is then used to infect target cells in which the vector genome and any carried marker or therapeutic genes becomes integrated into the target cell's DNA. A cell infected with such a recombinant viral particle cannot produce new vector virus since no viral proteins are present in these cells. However, the DNA of the vector carrying the therapeutic and marker genes is integrated in the cell's DNA and can now be expressed in the infected cell.

The recombinant MVA virus according to the invention expressing T7 RNA polymerase can be used to produce the proteins required for packaging retroviral vectors. To do this the gag, pol and env genes of a retrovirus (e.g. the Murine Leukemia Virus (MLV)) are placed under transcriptional control of a T7 RNA polymerase promoter in one or more expression vectors (e.g. plasmids). The expression vectors are then introduced into cells infected with the recombinant MVA virus expressing T7 RNA polymerase, together with an expression vector carrying a retroviral vector construct, possibly under transcriptional control of a T7 RNA polymerase promoter.

WO 94/2943 7, WO 89/11539 and WO 96/7748 describes different types of retroviral vector which can be packaged using the packaging system described above.

A further use of the recombinant MVA virus expressing T7 RNA polymerase is to generate recombinant proteins, noninfectious virus particles, or infectious mutant virus particles for the production of vaccines or therapeutics (Buchholz et al., *Virology,* 204:770-776 (1994) and EP-B1-1356695)). To do this viral genes (e.g. the gag-pol and env genes of HIV-1) are placed under transcriptional control of the T7 promoter in an expression vector (e.g. plasmid or another recombinant MVA virus). This construct is then introduced into cells infected with the recombinant MVA virus expressing T7 RNA polymerase. The recombinant viral genes are transcribed with high efficiency, recombinant proteins are made in high amounts and can be purified. Additionally, expressed recombinant viral proteins (e.g., HIV-1 env, gag) may assemble to viral pseudo-particles that budd from the cells and can be isolated from the tissue culture medium. In another embodiment, viral proteins (from e.g. HIV, SIV, Measles virus) expressed by the MVA-T7 pol system may rescue an additionally introduced mutant virus (derived from e.g. HIV, SIV, Measles virus) by overcoming a defect in attachment and infection, uncoating, nucleic acid replication, viral gene expression, assembly, budding or another step in viral multiplication to allow production and purification of the mentioned mutant virus.

MVA-T7pol can also be used together with DNA sequences carrying the gene of an antigen of interest (e.g. the gene of HIV, nef, tat, gag, pol, or env or others) for immunization. First, a coding sequence of a given antigen (e.g HIV, HCV, HPV, HSV, measles virus, influenza virus or other) are cloned under control of a T7 RNA polymerase promoter preferably in a plasmid vector and the resulting DNA construct is amplified and purified using standard laboratory procedures. Secondly, the vector DNA is inoculated simultaneously or with appropriate limelags together with MVA-T7pol. At the site of inoculation the recombinant gene of interest is expressed transiently in cells containing both the vector DNA and MVA-T7 pol and the corresponding antigen is presented to the host immune system stimulating an antigen-specific immune response. This protocol using the non-replication vaccinia with MVA -T7 pol represents a promising novel approach to nucleic acid vaccination allowing efficient transient expression of a given antigen, but avoiding the potential risk of constitutive gene expression.

The Recombinant MVA Vaccinia Viruses can be Prepared as Set Out Hereinafter

A DNA-construct which contains a DNA-sequence which codes for a foreign polypeptide flanked by MVA DNA sequences adjacent to a naturally occurring deletion, e.g. deletion II, within the MVA genome, is introduced into cells infected with MVA, to allow homologous recombination.

Once the DNA-construct has been introduced into the eukaryotic cell and the foreign DNA has recombined with the viral DNA, it is possible to isolate the desired recombinant vaccinia virus in a manner known per se, preferably with the aid of a marker (compare Nakano et al., *Proc. Natl. Acad. Sci. USA,* 79:1593-1596 (1982); Franke et al., *Mol. Cell. Biol,* 1918-1924 (1985); Chakrabarfi et al., *Mol. Cell. Biol.,* 3403-3409 (1985); Fathi et al., *Virology* 97-105 (1986)).

The DNA-construct to be inserted can be linear or circular. A circular DNA is preferred, especially a plasmid. The DNA-construct contains sequences flanking the left and the right side of a naturally occurring deletion, e.g. deletion II, within the MVA genome (Altenburger, W., Suter, C. P. and Altenburger J., *Arch. Virol.,* 105:15-27 (1989)). The foreign DNA sequence is inserted between the sequences flanking the naturally occurring deletion. The foreign DNA sequence can be a gene coding for a therapeutic polypeptide, e.g. t-PA or interferon, or an antigenic determinant from a pathogenic agent. Pathogenic agents can be viruses, bacteria and parasites which may cause a disease, as well as tumor cells which multiply unrestrictedly in an organism and may thus lead to pathological growths. Examples of such pathogenic agents are described in Davis, B. D. et al., (Microbiology, 3rd ed., Harper international Edition). Preferred antigens of pathogenic agents are those of human immunodeficiency viruses (e.g. HIV-1 and HIV-2), of mycobacteria causing tuberculosis, of the parasite *Plasmodium Falciparum*, and of melanoma cells.

For the expression of a DNA sequence or gene, it is necessary for regulatory sequences, which are required for the transcription of the gene, to be present on the DNA. Such regulatory sequences (called promoters) are known to those skilled in the art, and includes for example those of the vaccinia 11 kDa gene as are described in EP-A-198,328, and those of the 7.5 kDa gene (EP-A-110,385).

The DNA-construct can be introduced into the MVA infected cells by transfection, for example by means of calcium phosphate precipitation (Graham et al., *Virol.,* 52:456-467 (1973); Wigler et al., *Cell* 777-785 (1979)) by means of electroporation (Neumann et al., *EMBO J.,* 1:841-845 (1982)), by microinjection (Graessmann et al., *Meth. Enzymol.* 101:482-492 (1983)), by means of liposomes (Straubinger et al., *Methods in Enzymology,* 101:512-527 (1983)), by means of spheroplasts (Schaffner, *Proc. Natl. Acad. Sci. USA,* 77:2163-2167 (1980)) or by other methods known to those skilled in the art. Transfection by means of calcium phosphate precipitation is preferred.

The detailed examples which follow are intended to contribute to a better understanding of the present invention. However, it is not intended to give the impression that the invention is confined to the subject-matter of the examples.

EXAMPLES

1. Growing and Purification of the Viruses 1.1 Growing of the MVA Virus

The MVA virus is a highly attenuated vaccinia virus derived from the vaccinia virus strain Ankara (CVA) by long-term serial passages on primary chicken embryo fibroblast (CEF) cultures. For a general review of the history of the production, the properties and the use of MVA strain, reference may be made to the summary published by Mayr et al., in *Infection*, 3:6-14 (1975). Due to the attenuation in CEF, the MVA virus replicates to high titers in this avain host cell. In mammalian cells, however, MVA is severely growth restricted, and typical plaque formation by the virus is not detectable. Therefore, MVA virus was grown on CEF cells. To prepare CEF cells, 11-day-old embryos were isolated from incubated chicken eggs, the extremities are removed, and the embryos are minced and dissociated in a solution composed of 0.25% trypsin at 37° C. for 20 minutes. The resulting cell suspension was filtered and cells were sedimented by centrifugation at 2000 rpm in a Sorvall RC-3B centrifuge at room temperature for 5 minutes, resuspended in 10 volumes of medium A (MEM Eagle, for example obtainable from Life Technologies GmbH, Eggenstein, Germany), and sedimented again by centrifugation at 2000 rpm in a Sorvall RC-3B centrifuge at room temperature for 5 minutes. The cell pellet was reconstituted in medium A containing 10% fetal calf serum (FCS), penicillin (100 units/ml), streptomycin (100 mg/ml) and 2 mM glutamine to obtain a cell suspension containing 500,000 cells/ml. CEF cells obtained in this way were spread on cell culture dishes. They were left to grow in medium A in a $CO_2$ incubator at 37° C. for 1-2 days, depending on the desired cell density, and were used for infection either directly or after one further cell passage. A detailed description of the preparation of primary cultures can be found in the book by R. I. Freshney, "Culture of animal cell, Alan R. Liss Verlag, New York (1983) Chapter 11, page 99 et seq.

MVA viruses were used for infection as follows. CEF cells were cultured in 175 $cm^2$ cell culture bottles. At 90-100% confluence, the medium was removed and the cells were incubated for one hour with an MVA virus suspension (0.01 infectious units (IU) per cell, 0.02 ml/$cm^2$) in medium A. Then more medium A was added (0.2 ml/$cm^2$) and the bottles were incubated at 37° C. for 2-3 days (until about 90% of the cells show cytopathogenic effect). Crude virus stocks were prepared by scraping cell monolayers into the medium and pelleting the cell material by centrifugation at 3000 rpm in a Sorvall RC-3B centrifuge at 4° C. for 5 minutes. The crude virus preparation was stored at −20° C. before processing (e.g., virus purification).

1.2 Purification of the Viruses

The purification steps undertaken to obtain a virus preparation which was as pure as possible and free from components specific to the host cell were similar to those described by Joklik, *Virology,* 18:9-18 (1962)). Crude virus stocks which had been stored at −20° C. were thawed and suspended once in PBS (10-20 times the volume of the sediment), and the suspension was centrifuged as above. The new sediment was suspended in 10 times the volume of Tris buffer 1 (10 mM Tris-HCl pH 9.0,), and the suspension was briefly treated with ultrasound (Labsonic L, B. Braun Biotech International, Melsungen Germany; 2×10 seconds at 60 watts and room temperature) in order to further disintegrate cell debris and to liberate the virus particles from the cellular material. The cell nuclei and the larger cell debris were removed in the subsequent brief centrifugation of the suspension (Sorvall GSA rotor obtainable from DuPont Co., D-6353 Bad Nauheim, FRG; 3 minutes at 3000 rpm and 10° C.). The sediment was once again suspended in Tris buffer 1, treated with ultrasound and centrifuged, as described above. The collected supernatants containing the free virus particles were combined and layered over a cushion of 10 ml of 36% sucrose in 10 mM Tris-HCl, pH 9.0, and centrifuged in a Beckman SW 27/SW 28 rotor for 80 minutes with 13,500 rpm at 40° C. The supernatant was discarded, and the sediment containing the virus particles was taken up in 10 ml of 1 mM Tris-HCl, pH 9.0, homogenized by brief treatment with ultrasound (2×10 seconds at room temperature, apparatus as described above), and applied to a 20-40% sucrose gradient (sucrose in 1 mM Tris-HCl, pH 9.0) for further purification. The gradient was centrifuged in Beckmann SW41 rotor at 13,000 rpm for 50 minutes at 4° C. After centrifugation, discrete bands containing virus particles were harvested by pipetting after aspirating volume above band. The obtained sucrose solution was diluted with three volumes PBS and the virus particles were sedimented again by centrifugation (Beckmann SW 27/28, 60 minutes at 13,500 rpm, 4° C.). The pellet, which now consisted mostly of pure virus particles, was resuspended in PBS and equilibrated to virus concentrations corresponding on average to $1-5\times10^9$ IU/ml. The purified virus stock solution was stored at $-80°$ C. and used either directly or diluted with PBS for subsequent experiments.

1.3 Cloning of MVA Virus

To generate homogeneous stock virus preparations MVA virus obtained from Prof. Anton Mayr was cloned by limiting dilution during three consecutive passages in CEF cultured on 96-well tissue culture plates. The MVA clone F6 was selected and amplified in CEF to obtain working stocks of virus that served as starting material for the generation of recombinant MVA viruses described in this patent application as well as for the generation of recombinant MVA viruses described previously (Sutter, G. and Moss, B., *Proc. Natl. Acad. Sci. USA*, 89:10847-10851 (1992); Sutter, G. et al., *Vaccine*, 12:1032-1040 (1994); Hirsch, V. et al., *J. Virol.*, 70:3741-3752 (1996)).

2. Construction and Characterization of Recombinant MVA Viruses 2.1. Construction of Vector Plasmids To allow the generation of recombinant MVA viruses novel vector plasmids were constructed. Insertion of foreign genes into the MVA genome was targeted precisely to the site of the naturally occurring deletion II in the MVA genome. Sequences of MVA DNA flanking the site of a 2500-bp deletion in the HindIII N fragment of the MVA genome (Altenburger, W. et al., *J. Arch. Virol.*, 105:15-27 (1989)) were amplified by PCR and cloned into the multiple cloning site of plasmid pUC18. The primers for the left 600-bp DNA flank were 5'-CAG CAG GGT ACC CTC ATC GTA CAG GAC GTT CTC-3' (SEQ ID NO: 1) and 5'-CAG CAG CCC GGG TAT TCG ATG ATT ATT TTT AAC AAA ATA ACA-3' (SEQ ID NO: 2) (sites for restriction enzymes KpnI and SmaI are underlined).

Figure 2:
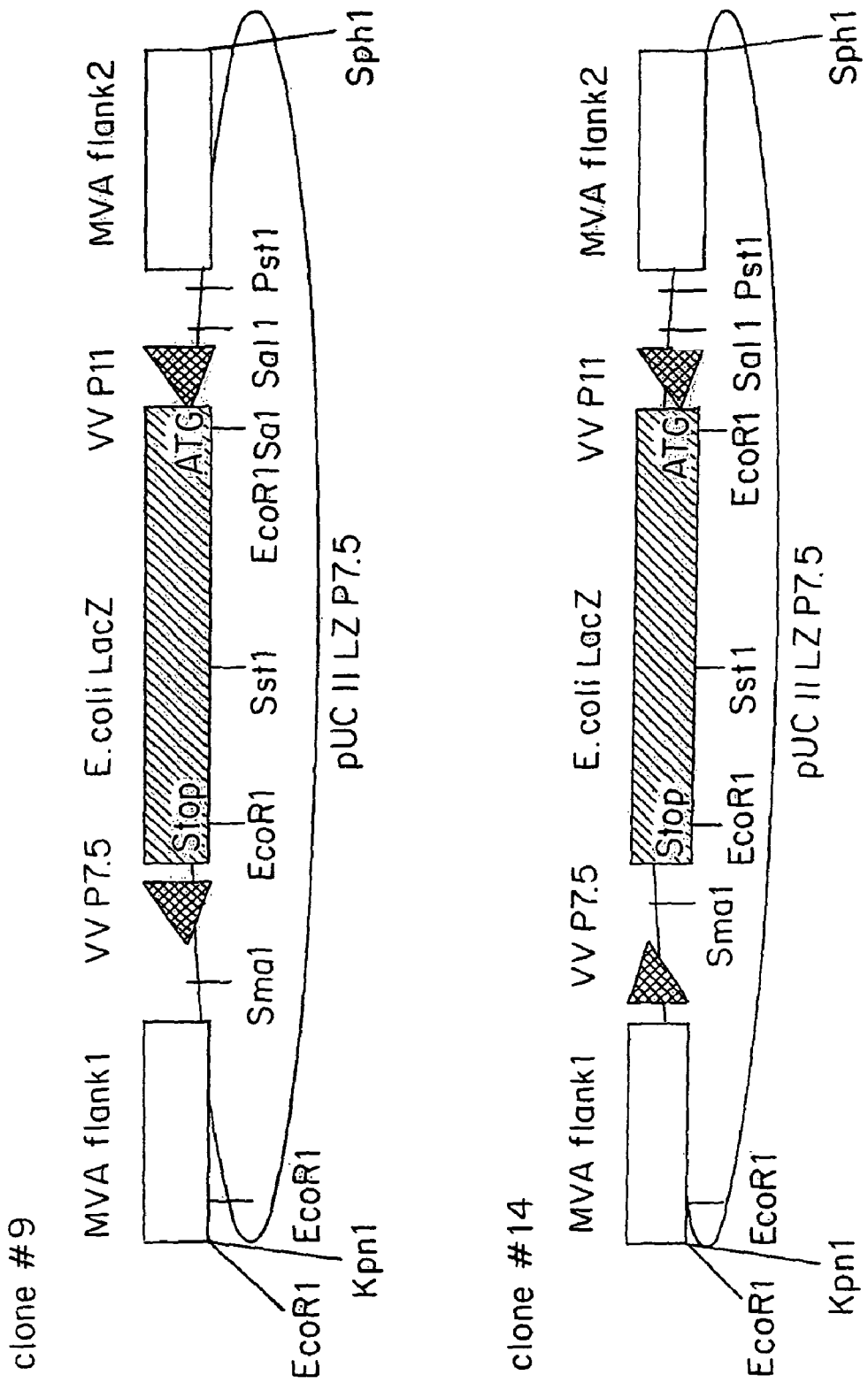
FIG. 2 is a schematic map of pUC II LZ P7.5: MVA vector plasmid for insertion into deletion II containing P11-LacZ expression cassette and the vaccinia virus early/late promoter P7.5 to express genes of interest that can be cloned into the SmaI site of the plasmid.
Figure 3:
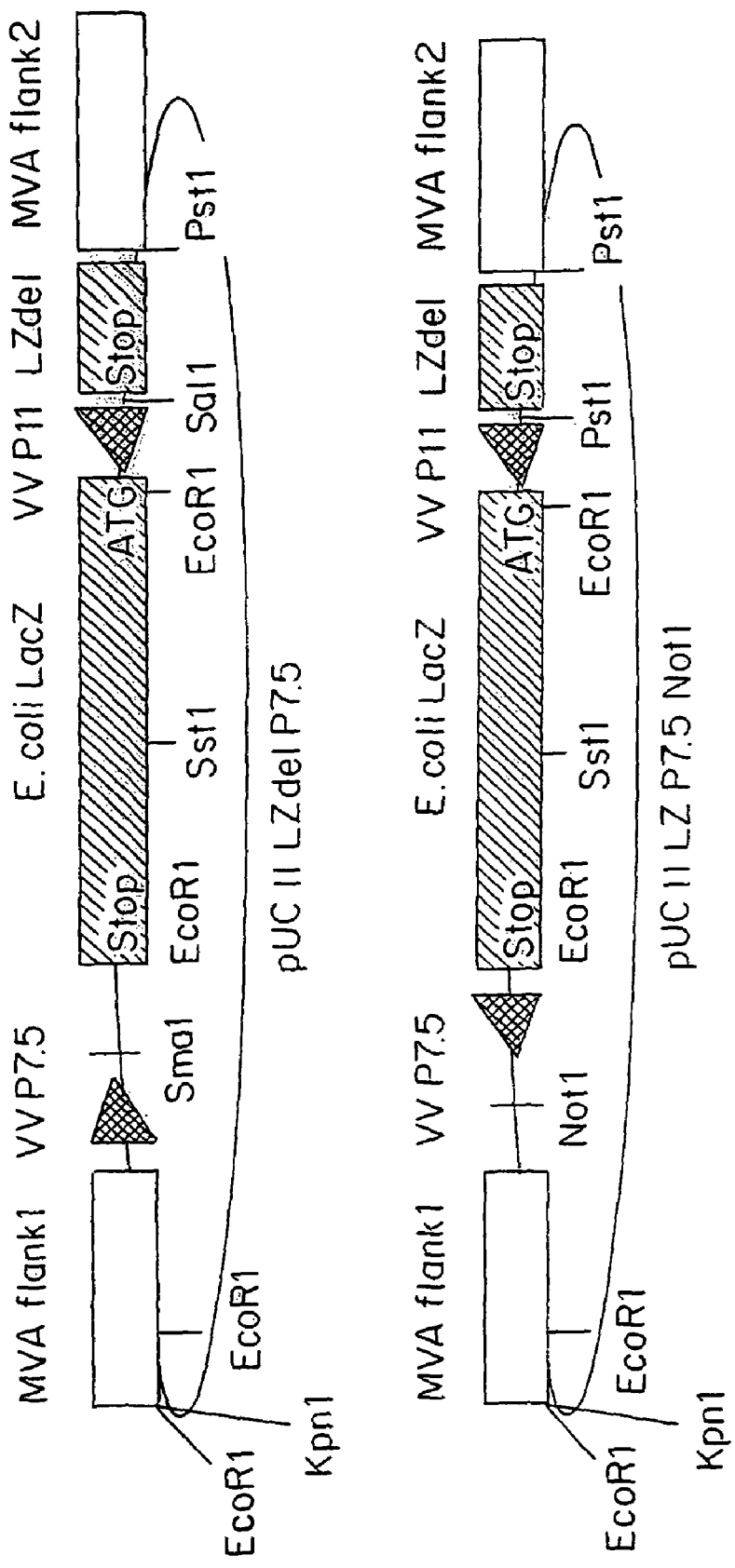
FIG. 3 is a schematic map of pUCII LZdel P7.5: MVA vector plasmid for insertion of foreign genes at the site of deletion II in the MVA genome, containing a self-deleting P11-LacZ expression cassette and the vaccinia virus early/late promoter P7.5 to express genes of interest that can be cloned into the SmaI/NotI cloning site of the plasmid.

The primers for the right 550-bp DNA flank were 5'-CAG CAG CTG CAG GAA TCA TCC ATT CCA CTG AAT AGC-3' (SEQ ID NO: 3); and 5'-CAG CAG GCA TGC CGA CGA ACA AGG AAC TGT AGC AGA-3' (SEQ ID NO: 4) (sites for restriction enzymes PstI and SphI are underlined). Between these flanks of MVA DNA inserted in pUC18, the *Escherichia coli* LacZ gene under control of the vaccinia virus late promoter P11 (prepared by restriction digest from pIII LZ, Sutter, G. and Moss, B., *PNAS USA* 89:10847-10851 (1992)) was inserted, using the BamHI site, to generate the MVA insertion vector pUCII LZ (FIG. 1). In the following, a 289 bp fragment containing the vaccinia virus early-late promoter P7.5 together with a SmaI site for cloning (prepared by restriction digest with EcoRI and XbaI from the plasmid vector pSC11 (Chakrabarbti et al., *Mole. Cell. Biol.*, 5:3403-3409 (1985)) was inserted into the SmaI site of pUCII LZ to give the MVA vector pUC II LZ P7.5 [FIG. 2]. To construct a vector plasmid that allows isolation of recombinant MVA viruses via transient synthesis of the reporter enzyme β-galactosidase a 330 bp DNA fragment from the 3'-end of the *E. coli* LacZ open reading frame was amplified by PCR (primers were 5'-CAG CAG GTC GAC CCC GAC CGC CTT ACT GCC GCC-3' (SEQ ID NO: 5) and 5'-GGG GGG CTG CAG ATG GTA GCG ACC GGC GCT CAG-3' (SEQ ID NO: 6)) and cloned into the SalL and PstI sites of pUC II LZ P7.5 to obtain the MVA vector pUC II LZdel P7.5 (FIG. 3). Using the SmaI site, this vector plasmid can be used to insert DNA sequences encoding a foreign gene under transcriptional control of the vaccinia virus promoter P7.5 into the MVA genome. After the desired recombinant virus has been isolated by screening for expression of β-galactosidase activity further propagation of the recombinant virus leads to the self-deletion of the reengineered P11-LacZ expression cassette by homologous recombination.

2.2. Construction and Characterization of Recombinant Virus MVA T7pol

Figure 4:
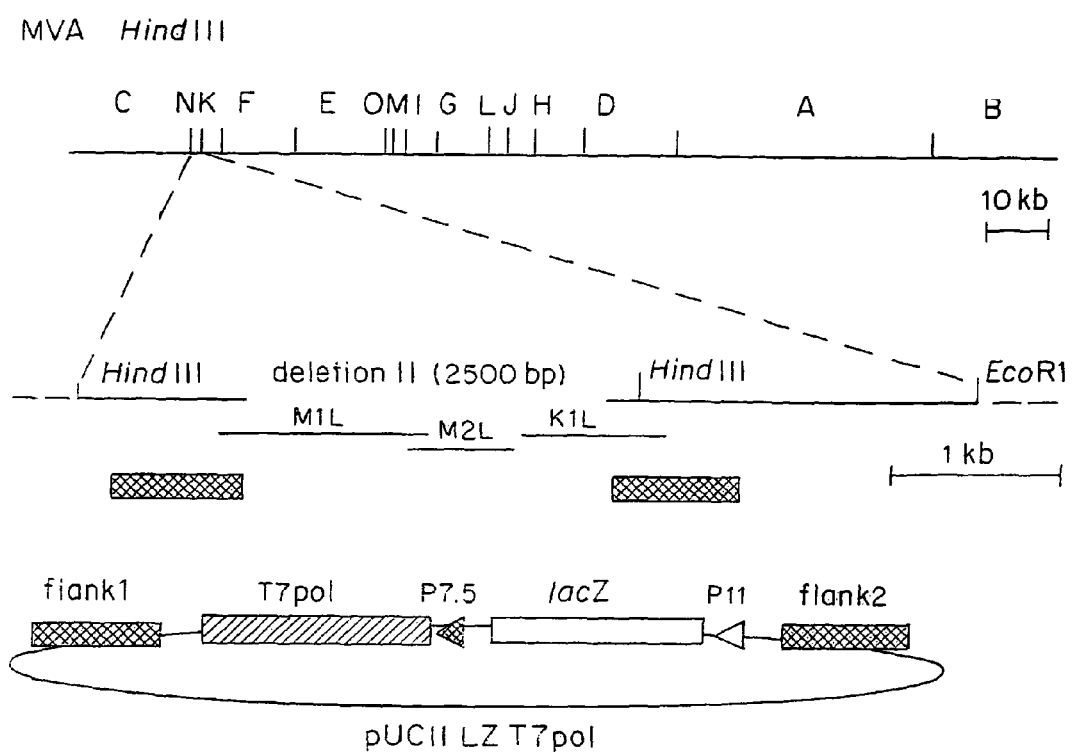
FIG. 4 is a schematic map of the construction of recombinant virus MVA-T7pol: schematic maps of the MVA genome (HindIII restriction endonuclease sites) and the vector plasmid pUC II LZ T7pol that allows insertion of the T7 RNA polymerase gene at the site of deletion II within the HindIII N fragment of the MVA genome.

A 3.1 kbp DNA fragment containing the entire gene of bacteriophage T7 RNA polymerase under control of the vaccinia virus early/late promoter P7.5 was excised with EcoRl from plasmid pTF7-3 (Fuerst, T. R. et al., *P.N.A.S. USA*, 83:8122-8126 (1986), modified by incubation with Klenow DNA polymerase to generate blunt ends, and cloned into a unique SmaI restriction site of pUCII LZ to make the plasmid transfer vector pUCII LZ T7pol (FIG. 4). As transcriptional regulator for the expression of the T7 RNA polymerase gene the vaccinia virus early/late promoter P7.5 was chosen. Contrary to stronger vaccinia virus late promoters (e.g. P11) this promoter system allows expression of recombinant genes immediately after the infection of target calls. The plasmid pUCII LZ T7pol that directs the insertion of the foreign-genes into the site of deletion II of the MVA genome was used to generate the recombinant virus MVA T7pol.

CEF cells infected with MVA at a multiplicity of 0.05 $TCID_{50}$ per cell were transfected with DNA of plasmid pUCII LZ T7pol as described previously (Sutter, G, et al., *Vaccine*, 12:1032-1040 (1994)). Recombinant MVA virus expressing the T7 RNA polymerase and co-expressing β-D-galactosidase (MVA P7.5-T7pol) was selected by five consecutive rounds of plaque purification in CEF cells stained with 5-bromo-4-chloro-3-indolyl β-D-galactoside (300 µg/ml). Subsequently, recombinant viruses were amplified by infection of CEF monolayers, and the DNA was analyzed by PCR to confirm genetic homogeneity of the virus stock. Southern blot analysis of MVA-T7pol viral DNA demonstrated stable integration of the recombinant genes at the site of deletion II within the MVA genome.

To monitor expression of T7 RNA polymerase by recombinant MVA T7pol [$^{35}$S]methionine -labeled polypeptides from virus infected tissue culture were analyzed. Monolayers of the monkey kidney cell line CV-1 grown in 12-well plates were infected with virus at a multiplicity of 20 $TCID_{50}$ per cell. At 3 to 5 hours after infection, the medium was removed, and the cultures were washed once with 1 ml of methionine free medium. To each well, 0.2 ml of methionine-free medium supplemented with 50 µCi of [$^{35}$S]methionine was added and incubated for 30 minutes at 37° C. Cytoplasmic extracts of infected cells were prepared by incubating each well in 0.2 ml of 0.5% Nonidet P-40 lysis buffer for 10 mm at 37° C. and samples were analyzed by SDS-PAGE. The metabolic labeling of the CV-1 cells with MVA T7pol revealed the synthesis of two additional polypeptides (i) a protein of about 116,000 Da representing the *E. coli* β-galactosidase co-expressed to allow the screening for recombinant virus and (ii) a 98,000 Da protein with the expected size of the bacteriophage T7 RNA polymerase. The large amount of β-galactocidase made by MVA T7pol is remarkable. The results from the in vivo labeling experiments demonstrate a very strong expression of the P11-LacZ gene construct when inserted into the MVA genome at the site of deletion II indicating that recombinant genes in MVA vector viruses might be expressed more efficiently when inserted into this locus of the MVA genome.

The usefulness of MVA-T7pol recombinant viruses as expression system in comparison to the WR-T7pol recombinant virus vTF7-3 (Fuerst et al. 1986) was tested by the co-transfection of DNA of a plasmid vector that is derived from pTM1 (Moss, B., et al., *Nature*, 348:91-92 (1990)) and contains (cloned into the NcoI and BamHI sites of the pTM 1 multiple cloning site) the *E. coli* chloramphenicol acetyltranferase (CAT) gene under the control of a T7 RNA polymerase promoter ($PT_7$). Transfected and infected CV-1 cells were suspended in 0.2 ml of 0.25 M Tris-HCl (pH 7.5). After three freeze-thaw cycles, the lysates were cleared by centrifugation, the protein content of the supernatants was determined, and samples containing 0.5, 0.25, 0.1 µg total protein were assayed for enzyme activity as described by Mackett, M., et al., *J. Virol.*, 49:857-864 (1984). After autoradiography, labeled spots were quantitated using the Fuji imaging analysis system.

The results demonstrate that by using the highly attenuated vaccinia vector MVA it is possible to exploit the vaccinia virus-T7 RNA polymerase system as efficiently as by using a fully replication-competent vaccinia virus recombinant.

2.3. Construction and Characterization of Recombinant Virus MVA-LAInef

Figure 5:
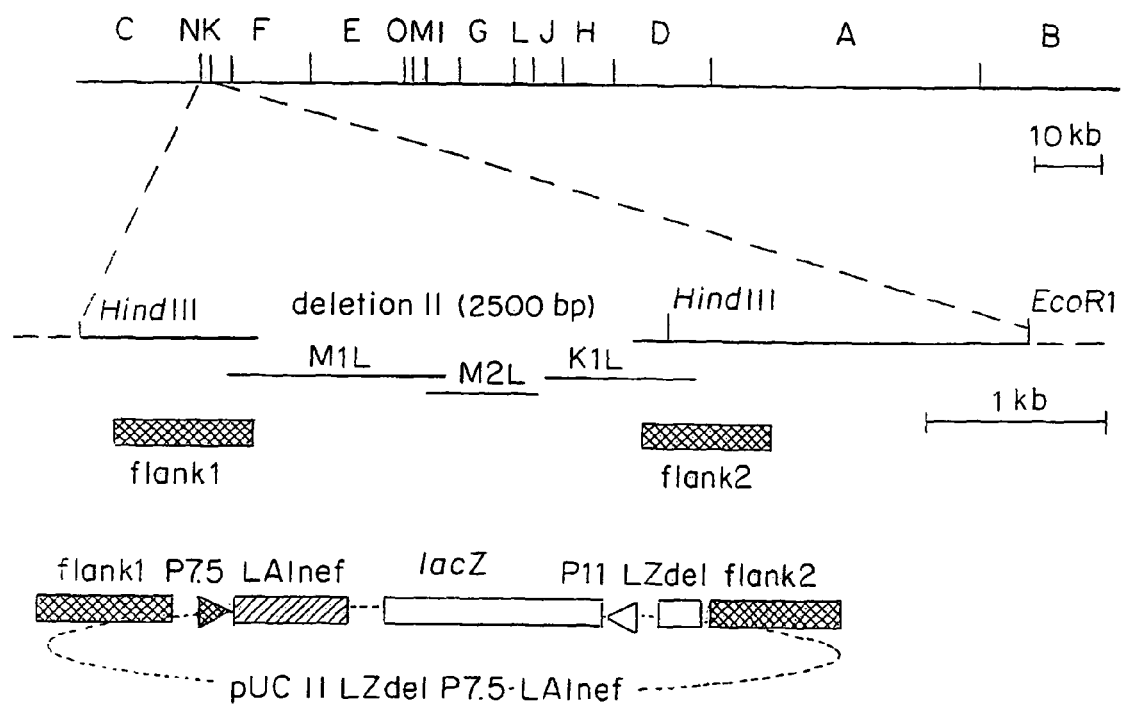
FIG. 5 is a schematic map of the construction of MVA-LAInef: schematic maps of the MVA genome (HindIII restriction endonuclease sites) and the vector plasmid pUC II LZdel P7.5-LAInef that allows insertion of the nef gene of HIV-1 LAI at the site of deletion II within the HindIII N fragment of the MVA genome.

A 648 bp DNA fragment containing the entire nef gene of HIV-1 LAI was prepared by PCR from plasmid DNA (pTG1166 kindly provided by M.-P. Kieny, Transgene S. A., Strasbourg; PCR primers were 5'-CAG CAG GGA TCC ATG GGT GGC AAG TGG TCA AAA AGT AGT-3' (SEQ ID NO: 7) and 5'-CAG CAG GGA TCC ATG TCA GCA GTT CTT GAA GTA CTC CGG-3' (SEQ ID NO: 8)), digested with restriction endonuclease BamHI, modified by incubation with Klenow DNA polymerase to generate blunt ends, and cloned into the SmaI site of pUC II LZdel P7.5 to make the vector pUC II LZdel P7.5-LAInef (FIG. 5). This plasmid could be used to engineer MVA recombinant virus that expresses the nef gene of HIV-1 LAI under control of the vaccinia virus early/late promoter P7.5.

CEF cells infected with MVA at a multiplicity of 0.05 $TCID_{50}$ per cell were transfected with DNA of plasmid pUC II LZdel P7.5-LAInef as described previously (Sutter, G. et al., *Vaccine*, 12:1032-1040 (1994)). Recombinant MVA viruses containing the nef gene and transiently co-expressing the *E. coli* LacZ marker gene were selected by consecutive rounds of plaque purification in CEF cells stained with 5-bromo-4-chloro-3-indolyl β-D-galactoside (300 µg/ml). In the following, recombinant MVA viruses containing the nef gene and having deleted the LacZ marker gene were isolated by three additional consecutive rounds of plaque purification screening for non-staining viral foci in CEF cells in the presence of 5-bromo-4-chloro-3-indolyl β-galactoside (300 µg/ml). Subsequently, recombinant viruses were amplified by infection of CEF monolayers, and the MVA-LAInef viral DNA was analyzed by PCR to confirm genetic homogeneity of the virus stock. Southern blot of viral DNA confirmed genetic stability of MVA-LAInef and precisely demonstrated integration of the nef gene and deletion of the *E. coli* LacZ marker gene at the site of deletion II within the viral genome.

Efficient expression of recombinant Nef protein was confirmed by Western blot analysis of protein lysates from CEF cells infected with MVA-LAInef using mouse monoclonal antibodies directed against HIV-1 Nef (kindly provided by K. Krohn and used as described by Ovod, V. et al., *AIDS*, 6:25-34 (1992)).

2.4. Construction and Characterization of Recombinant Virus MVA-hTYR

Figure 6:
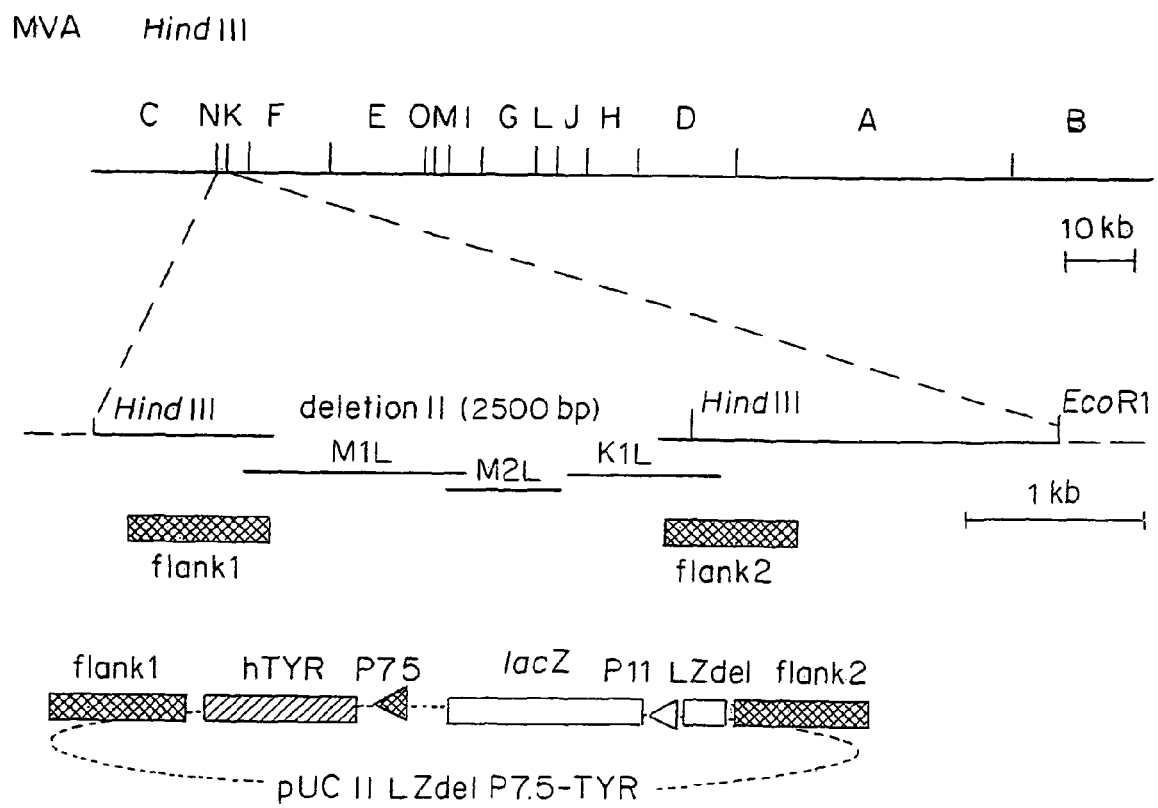
FIG. 6 is a schematic map of the construction of MVA-hTYR: schematic maps of the MVA genome (HindIII restriction endonuclease sites) and the vector plasmid pUC II LZdel P7.5-TYR that allows insertion of the human tyrosinase gene at the site of deletion II within the HindIII N fragment of the MVA genome.

A 1.9 kb DNA fragment containing the entire gene encoding human tyrosinase (Tyrosinase c-DNA clone 123.B2 isolated from the melanome cell line SK29-MEL of patient SK29 (AV), GenBank Acct. No. U01873; Brichard, V. et al., *J. Exp. Med.*, 178:489-495 (1993)) was prepared from the plasmid pcDNAI/Amp-Tyr (Wolfel, T. et al., *Eur. J. Immunol.*, 24:759-764 (1994)) by EcoRI digest, modified by incubation with Klenow DNA polymerase to generate blunt ends, and cloned into the SmaI site of pUC II LZdel P7.5 to make the vector pUC II LZdel P7.5-TYR (FIG. 6).

This plasmid could be used to engineer MVA recombinant virus that expresses the human tyrosinase gene under control of the vaccinia virus early/late promoter P7.5.

CEF cells infected with MVA at a multiplicity of 0.05 $TCID_{50}$ per cell were transfected with DNA of plasmid pUC II LZdel P7.5-TYR as described previously (Sutter, G, et al., *Vaccine*, 12:1032-1040 (1994)). Recombinant MVA virus stably expressing the gene for human tyrosinase and transiently co-expressing the *E. coli* LacZ gene was selected by consecutive rounds of plaque purification in CEF cells stained with 5-bromo-4-chloro-3-indolyl β-D-galactoside (300 µg/ml). In the following, recombinant MVA virus expressing the gene encoding human tyrosinase and having deleted the LacZ marker gene was isolated by three additional consecutive rounds of plaque purification screening for non-staining viral foci in CEF cells in the presence of 5-bromo-4-chloro-3-indolyl β-D-galactoside (300 µg/ml). Subsequently, recombinant viruses were amplified by infection of CEF monolayers, and the MVA-hTYR viral DNA was analyzed by PCR to confirm genetic homogeneity of the virus stock. Southern blot analysis of viral DNA confirmed genetic stability of MVA-hTYR and precisely demonstrated integration of the recombinant tyrosinase gene and deletion of the *E. coli* LacZ marker gene at the site of deletion II within the viral genome.

Efficient expression of recombinant human tryosinase was confirmed by Western blot analysis of protein lysates from CEF cells infected with MVA-hTYR using rabbit polyclonal antibodies (kindly provided by V. Hearing and used as described by Jimenez, M., et al., *P.NA.S. USA*, 85:3830-3834 (1988)) or mouse monoclonal antibodies (kindly provided by L. Old and used as described by Chen, Y. et al., *P.N.A.S. USA* 92:8125-8129 (1995)) directed against tyrosinase.

EQUIVALENTS

While this invention has been particularly shown and described with references to preferred embodiments thereof, it will be understood by those skilled in the art that various changes in form and details may be made therein without

What is claimed is:

1. An immunogenic composition comprising a Modified Vaccinia Virus Ankara (MVA) containing a foreign gene encoding an antigen against which an immune response is desired,
wherein the foreign gene is inserted at a site of a naturally occurring deletion within an MVA genome selected from the group consisting of deletion site I, site II, site IV, site V, and site VI.

2. The immunogenic composition of claim 1, wherein the site of a naturally occurring deletion within an MVA genome is deletion site I.

3. The immunogenic composition of claim 1, wherein the site of a naturally occurring deletion within an MVA genome is deletion site II.

4. The immunogenic composition of claim 1, wherein the site of a naturally occurring deletion within an MVA genome is deletion site IV.

5. The immunogenic composition of claim 1, wherein the site of a naturally occurring deletion within an MVA genome is deletion site V.

6. The immunogenic composition of claim 1, wherein the site of a naturally occurring deletion within an MVA genome is deletion site VI.

7. The immunogenic composition of claim 1, wherein the foreign gene is under the control of a T7 RNA polymerase promoter.

8. The immunogenic composition of claim 1, wherein the foreign gene is under the control of the vaccinia virus early/late promoter p7.5.

9. The immunogenic composition of claim 1, wherein the foreign gene is HIV-1 nef.

10. The immunogenic composition of claim 1, wherein the foreign gene is human tyrosinase.

* * * * *